United States Patent
Lauro

(10) Patent No.: US 7,831,313 B2
(45) Date of Patent: Nov. 9, 2010

(54) LEAD ANCHOR FOR IMPLANTABLE STIMULATION DEVICES AND METHODS OF MANUFACTURE AND USE

(75) Inventor: Reno B. Lauro, Garland, TX (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 609 days.

(21) Appl. No.: 11/213,265

(22) Filed: Aug. 26, 2005

(65) Prior Publication Data

US 2007/0050005 A1    Mar. 1, 2007

(51) Int. Cl.
*A61N 1/375* (2006.01)

(52) U.S. Cl. .................. 607/126; 604/174; 607/119; 24/136 R; 24/537

(58) Field of Classification Search .............. 604/174, 604/175, 178, 179; 607/119, 126, 130; 24/136 R, 24/537
See application file for complete search history.

(56) References Cited

U.S. PATENT DOCUMENTS

| | | | | |
|---|---|---|---|---|
| 297,155 A | * | 4/1884 | Osgood | ..................... 24/136 R |
| 3,952,377 A | * | 4/1976 | Morell | ..................... 24/136 R |
| 4,672,979 A | * | 6/1987 | Pohndorf | ..................... 607/126 |
| 4,820,274 A | * | 4/1989 | Choksi et al. | ................ 604/174 |
| 5,152,298 A | * | 10/1992 | Kreyenhagen et al. | ...... 607/116 |
| 5,242,431 A | * | 9/1993 | Kristiansen | ................. 607/126 |
| 5,273,053 A | * | 12/1993 | Pohndorf | ..................... 604/175 |
| 5,682,796 A | * | 11/1997 | Malone | ..................... 24/136 R |
| 5,746,722 A | * | 5/1998 | Pohndorf et al. | ............ 604/175 |
| 6,058,574 A | * | 5/2000 | Facey et al. | ................ 24/136 R |
| 6,181,969 B1 | | 1/2001 | Gord | |
| 6,516,227 B1 | * | 2/2003 | Meadows et al. | ............ 607/117 |
| 6,572,588 B1 | * | 6/2003 | Bierman et al. | ............. 604/174 |
| 6,609,029 B1 | | 8/2003 | Mann et al. | |
| 6,609,032 B1 | | 8/2003 | Woods et al. | |
| 6,741,892 B1 | | 5/2004 | Meadows et al. | |
| 2004/0059392 A1 | | 3/2004 | Parramon et al. | |
| 2007/0078399 A1 | * | 4/2007 | Olson | ......................... 604/175 |

* cited by examiner

*Primary Examiner*—Scott M Getzow
*Assistant Examiner*—Joseph M Dietrich
(74) *Attorney, Agent, or Firm*—Frommer Lawrence & Haug LLP; Bruce E. Black

(57) ABSTRACT

A lead anchor includes a body defining a first opening and a second opening through which a lead can pass. A protrusion and a corresponding depression may be provided within the body that cooperate to form a non-linear path for the lead through the housing to resist movement of the lead within the lead anchor.

20 Claims, 7 Drawing Sheets

LEAD ANCHOR FOR IMPLANTABLE STIMULATION DEVICES AND METHODS OF MANUFACTURE AND USE

FIELD

The invention is directed to lead anchors for implantable devices, as well as the implantable devices themselves, and methods of manufacture and use of the lead anchors and implantable devices. The invention is also directed to lead anchors for implantable spinal cord stimulators, as well as the implantable spinal cord stimulators, and methods of manufacture and use of the lead anchors and the implantable spinal cord stimulators.

BACKGROUND

Spinal cord stimulation is a well accepted clinical method for reducing pain in certain populations of patients. Implantable stimulation devices have been developed to provide therapy for a variety of treatments. For example, implantable stimulation devices can be used to stimulate nerves, such as the spinal cord, muscles, or other tissue. An implantable stimulation device typically includes an implanted control module (with a pulse generator), a lead, and an array of stimulator electrodes. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

The stimulator electrodes are coupled to the control module by the lead and the control module is implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module. Many conventional leads anchors do not sufficiently grip the lead to keep the lead in place. One measure of the gripping ability of a lead anchor is the ability to hold the lead steady when a pulling force of 0.6 to 1 lb (about 2 to 5 N) is applied.

BRIEF SUMMARY

One embodiment is a lead anchor including a body defining a first opening and a second opening through which a lead can pass. A protrusion and a corresponding depression are provided within the body that cooperate to form a non-linear path for the lead through the housing to resist movement of the lead within the lead anchor.

Another embodiment is an implantable stimulation device that includes a control module; an electrode array; a lead coupling the control module to the electrode array; and at least one lead anchor disposed around a portion of the lead. The lead anchor includes a body defining a first opening and a second opening through which the lead can pass; and a protrusion and a corresponding depression within the body that cooperate to form a non-linear path for the lead through the housing to resist movement of the lead within the lead anchor.

Yet another embodiment is a method of implanting an implantable stimulation device by implanting an electrode array near tissue to be stimulated and implanting a control module. The electrode array is coupled to the control module using a lead and the lead is anchored to the surrounding tissue using a lead anchor. The lead anchor includes a body defining a first opening and a second opening through which the lead can pass and a protrusion and a corresponding depression within the body that cooperate to form a non-linear path for the lead through the housing to resist movement of the lead within the lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of lead anchors used with elongate implantable devices such as spinal cord leads, cardiac pacing leads or catheters, implantable devices or systems containing the lead anchors, methods of use and manufacture of lead anchors and implantable devices. In addition, the invention is directed to lead anchors for implantable spinal cord stimulators, as well as the stimulators themselves and methods of use and manufacture of the lead anchors and spinal cord stimulators.

A lead anchor can be used in an implantable device, such as an implantable spinal cord stimulator, to anchor a lead connecting a control module to an electrode array. The lead passes through the lead anchor along a non-linear (for example, curved) path to prevent or reduce the likelihood that the lead will move within the lead anchor. Preferably, the lead anchor applies gentle compression to the lead to hold the lead in place. The non-linear (for example, curved) path can be created using, for example, one or more pairs of opposing protrusions and depressions in the interior of the lead anchor to direct the lead along the non-linear (for example, curved) path.

Figure 1:
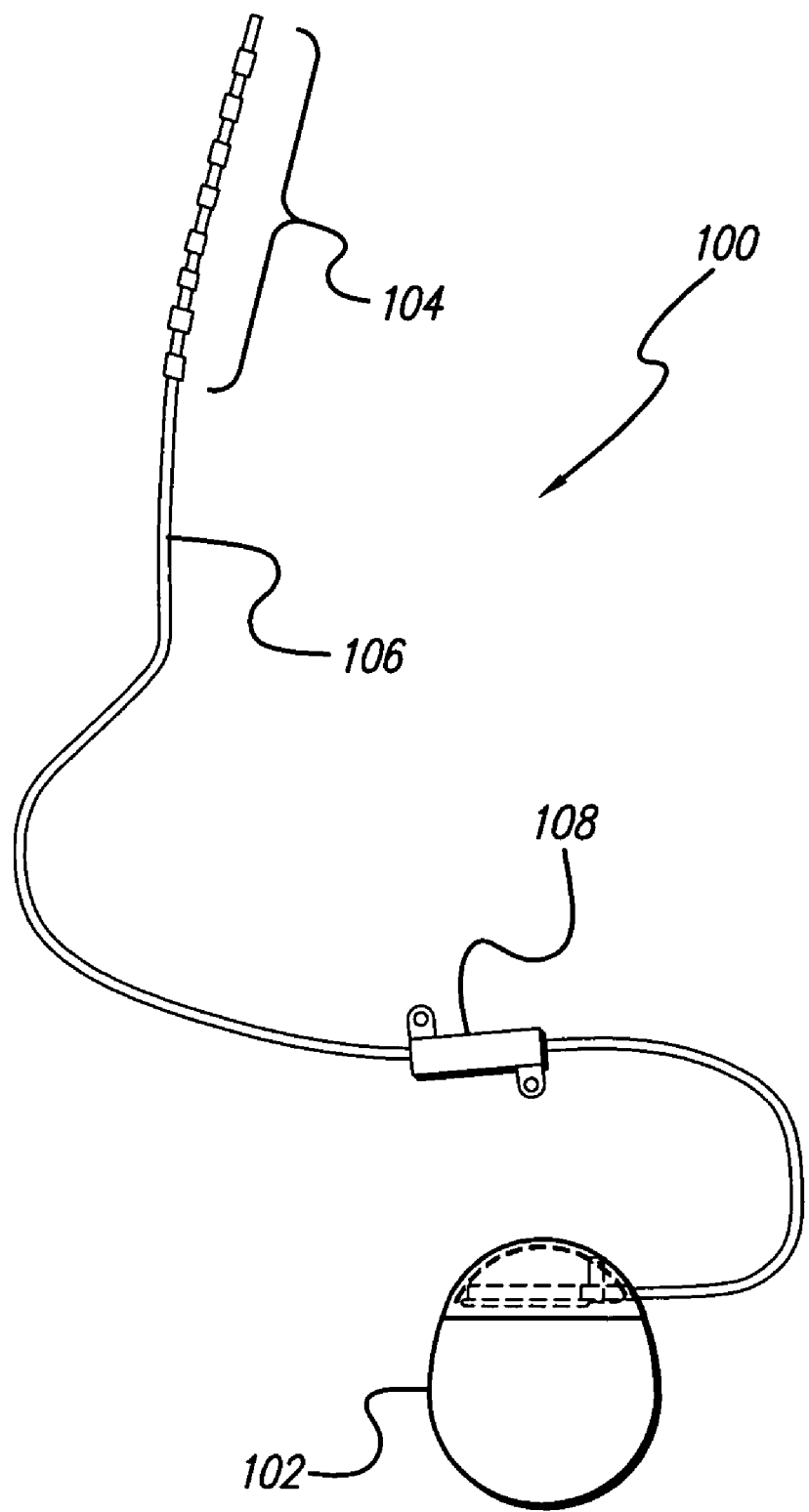
FIG. 1 is a schematic plan view of an implantable stimulator arrangement, according to the inventions.

FIG. 1 illustrates schematically an implantable stimulation device 100, such as a spinal cord stimulator. The implantable stimulation device includes a control module 102, an electrode array 104, a lead 106 coupling the control module to the electrode array, and one or more lead anchors 108. The control module 102 typically includes a pulse generator that provides pulses of stimulation current to electrodes of the electrode array 104. The control module 102 may also include a power source for generating the stimulation current or may receive power from an external source. The power source can be any available power source including batteries, such as primary batteries or rechargeable batteries. Examples of other power sources include, but are not limited to, super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

The control module 102 is optionally programmable to allowing programming of one or more functions such as, for example, the selection of electrodes for stimulation, the selection of electrodes as anode or cathode, the amplitude of the stimulation current, the duration of the stimulation current, and the periodicity of the stimulation current. In some embodiments, the control module 102 can be accessed using a programming unit external to the body of the patient to alter or modify these functions.

The electrode array 104 typically includes two or more electrodes. In some embodiments, the electrode array includes four, six, eight, 10, 16, or more electrodes. This electrodes can be in a linear array, for example, disposed along an electrode lead, or in a two-dimensional array, for example, forming two or more columns or rows, or any other arrangement. Non-limiting examples of suitable electrode arrays are illustrated in U.S. Pat. No. 6,516,227, incorporated herein by reference.

The lead 106 includes a set of conductors (for example, one conductor per electrode of the electrode array) within a non-conductive sheathing. Each conductor couples one or more electrodes to each output node of the control module. Non-limiting examples of suitable control modules, electrode arrays, and leads are illustrated in U.S. Pat. Nos. 6,181,969; 6,516,227; 6,609,029; 6,609,032; and 6,741,892, all of which are incorporated by reference.

Other common, elongate implantable devices include cardiac pacing leads, which typically may have one or two electrodes on the lead. Still other elongate devices include various implantable catheters. For example, one type of catheter is a drug delivery catheter for delivering drugs from a drug pump device attached to the delivery catheter. Any flexible, elongate implantable lead or catheter, including those described may be attachable with an embodiment of the lead anchor herein described.

One or more lead anchors can be used to attach the lead to surrounding tissues to prevent or resist movement of the lead within the body of the patient when the lead anchor is attached to surrounding tissue. FIGS. 2-7 illustrate one embodiment of a lead anchor 108. The lead anchor includes a body 120 that is open at two ends 122, 124 to allow the lead 106 to pass through the lead anchor. In the illustrated embodiment, the body 120 has two parts: an outer housing 126 and an inner sleeve 128. The outer housing and inner sleeve are movably engaged allowing the inner sleeve to move within the outer housing and to extend at least partially out of the outer housing, as illustrated, for example, in FIGS. 3, 4A, and 6. For example, the outer housing and inner sleeve can be slidably engaged to allow the inner sleeve to slide within the outer housing and allow at least a portion of the inner sleeve to extend out of the outer housing.

In the illustrated embodiment, the inner sleeve 128 is formed of two separate members 130, 132 that oppose each other across the interior of the body 120. In other embodiments, these members 130, 132 can be connected along a portion of the inner sleeve (typically, along the portion nearer opening 124.) The inner sleeve 128 is disposed within the outer housing 126 so that as the inner sleeve 128 moves and extends out of the outer housing 126, the two members 130, 132 spread away from each other, as illustrated, for example, in FIGS. 3, 4A, and 6, to permit easier access for threading the lead through the lead anchor 108.

A depression 134 (FIG. 3) is defined on the interior surface of member 132 and a protrusion 136 (FIG. 4A) is defined on the interior surface of member 130 opposite the depression 134. It will be understood that embodiments of the invention can include multiple depressions and protrusions and that the multiple depressions can all be defined on the same member (e.g., member 132) or can be distributed between the members 130, 132 with the corresponding protrusions opposing the depressions on the opposite member. The depression 134 may be complementary in shape to the protrusion 136 or may be larger or smaller than the protrusion 136. When the inner sleeve 128 is within the outer housing 126, the protrusion(s) 136 and depression(s) 134 form a non-linear (for example, curved) path for the lead 106 to traverse through the lead anchor, as illustrated, for example, in FIG. 7. Preferably, the lead is gently compressed and/or its path is deformed between the protrusion(s) 136 and depression(s) 134. The compression and/or path deformation is preferably sufficient to hold the lead firmly without damaging any of the conductors or sheathing of the lead or causing shorts between conductors. The non-linear (for example, curved) path formed by the protrusions 136 and depressions 134 prevents or inhibits the movement of the lead within the lead anchor and prevents or inhibits the removal of the lead from the lead anchor. When the lead anchor is attached to the surrounding tissue, the lead is held firmly in place.

Figure 7:
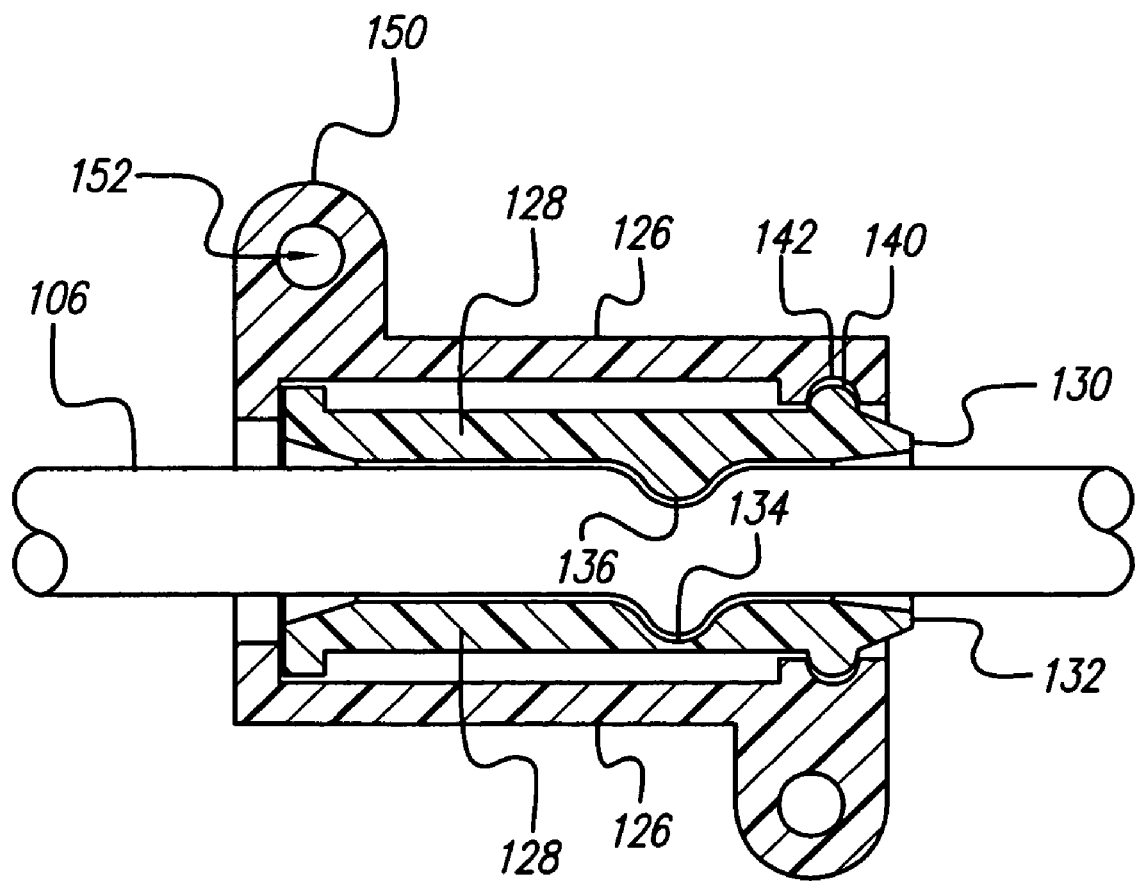
FIG. 7 is a schematic cross-sectional view of the lead anchor of FIG. 2 with the lead inserted and held by the lead anchor.

Optionally, an inner surface of the outer housing 126 and an outer surface of the inner sleeve 128 include a locking arrangement to lock the inner sleeve and outer housing and prevent or resist movement of the inner sleeve within the outer housing after the lead has been threaded through the lead anchor. One example of a locking arrangement includes a locking projection 140 formed on the outer surface of the inner sleeve 128 and a locking indentation 142 formed on the inner surface of the outer housing 126. It will be recognized that the locking projection could be positioned on the inner surface of the outer housing and the locking indentation could be formed on the outer surface of the inner sleeve. In operation, the inner sleeve 128 is pushed into the outer housing 126 until the locking projection 140 engages the locking indentation, as illustrated in FIG. 7. The inner sleeve is then locked into the outer housing. The locking arrangement can be released by, for example, squeezing the ends of the inner sleeve together to remove the locking projection from the locking indentation and then sliding the inner sleeve within the outer housing so that the locking projection no longer engages the locking depression.

Figure 2:
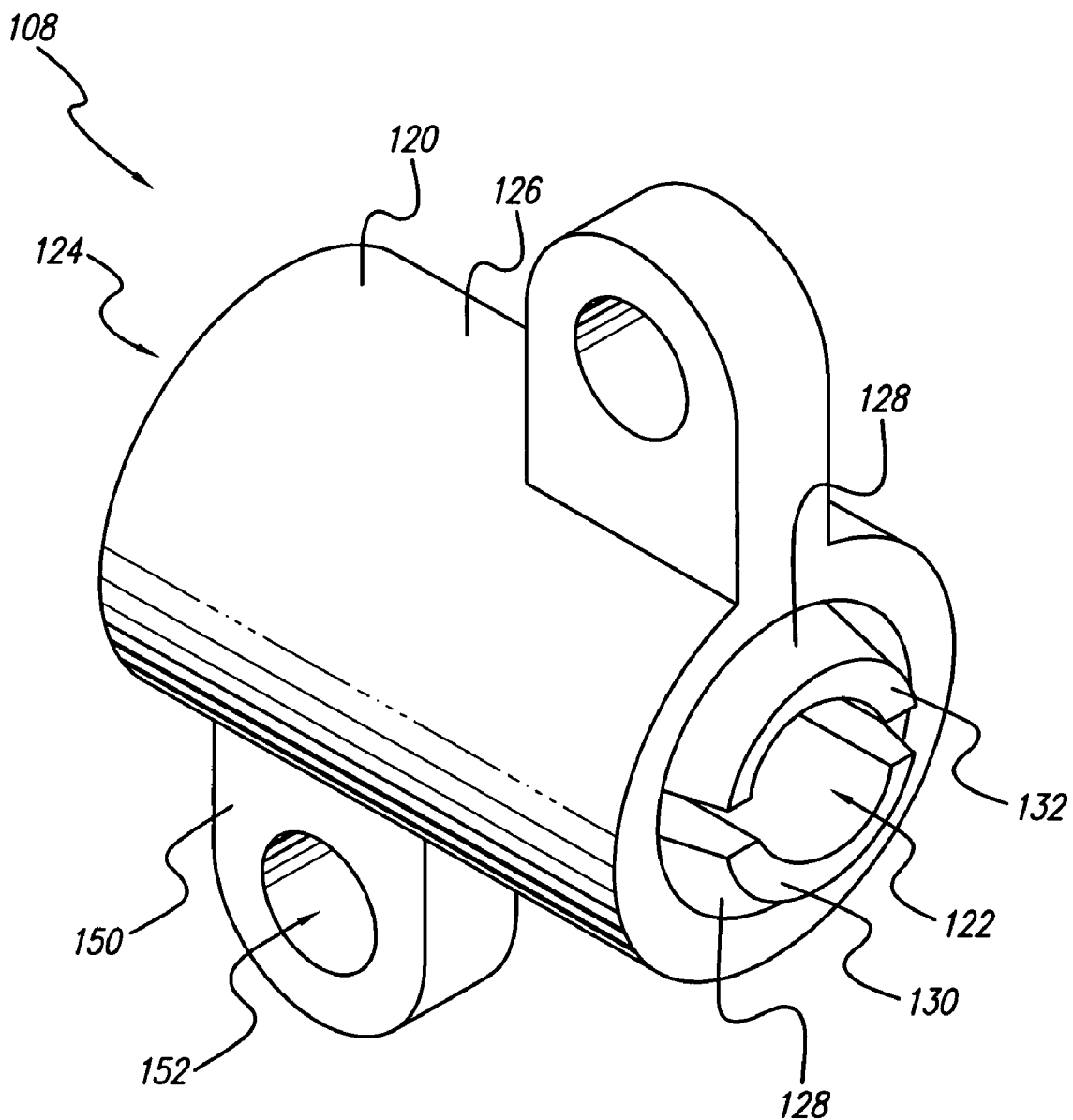
FIG. 2 is a schematic exterior perspective view of one embodiment of a lead anchor, according to the invention.
Figure 3:
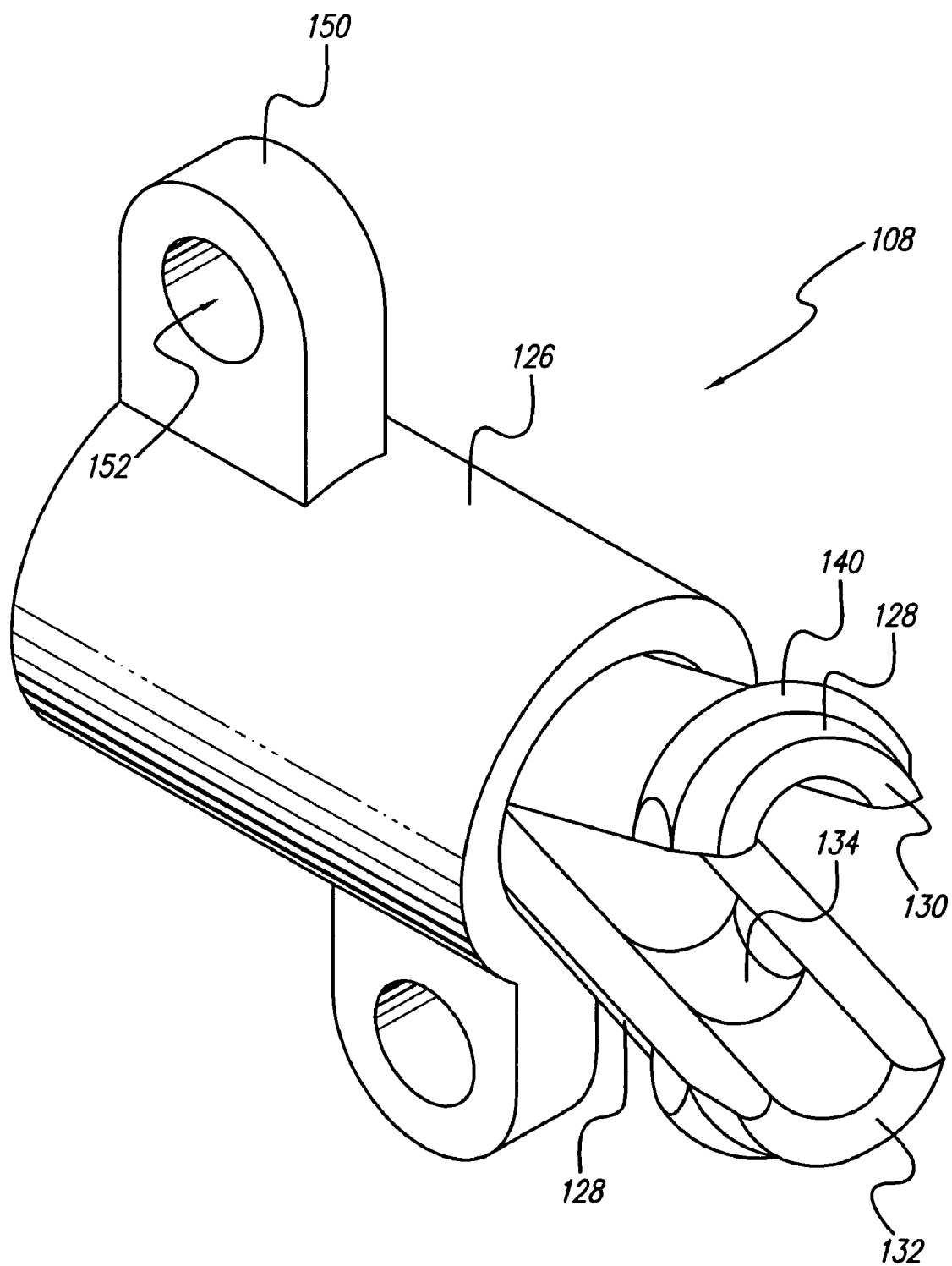
FIG. 3 is a schematic exterior perspective view of the lead anchor of FIG. 2 with the inner sleeve extended.
Figure 4A:
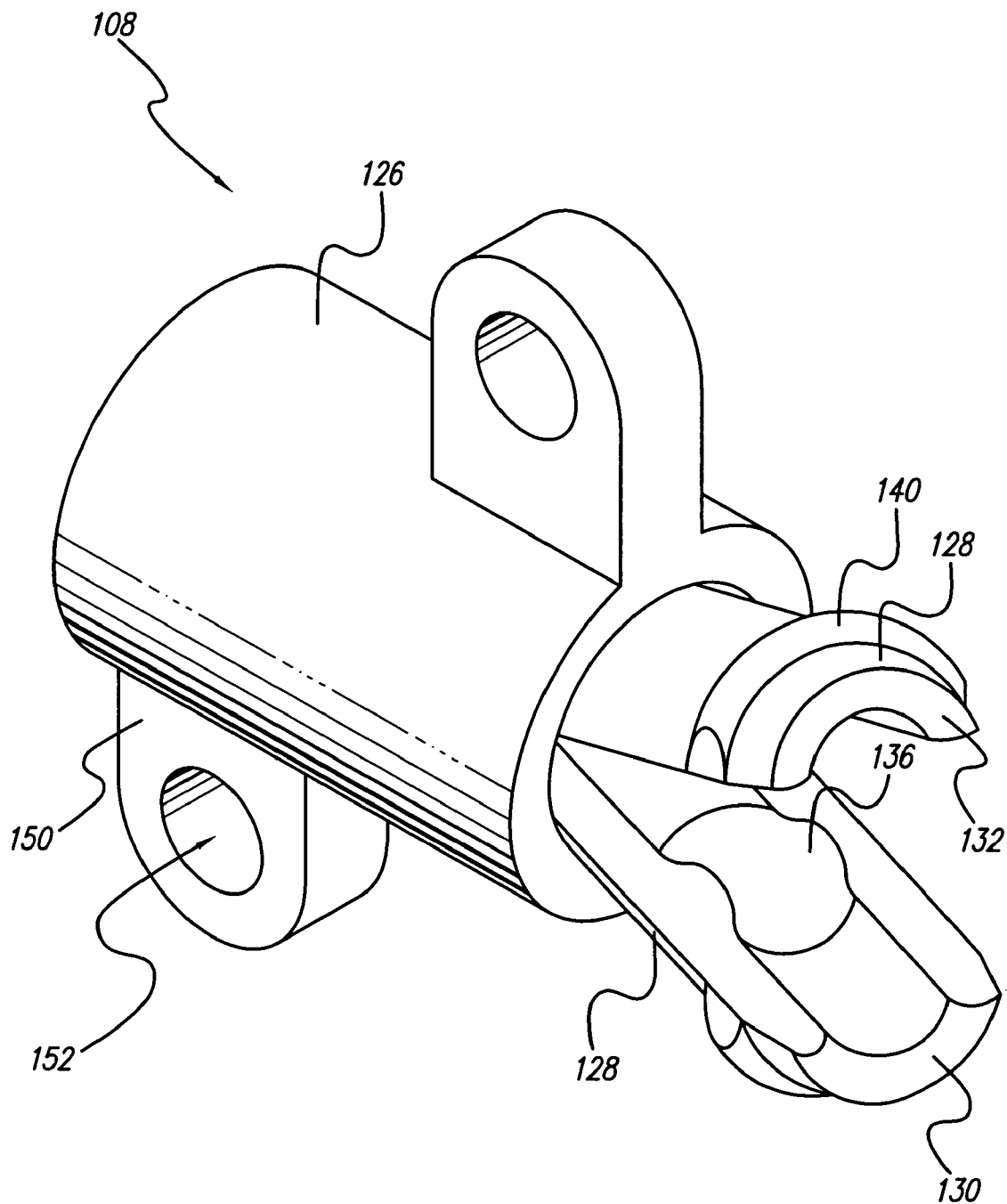
FIG. 4A is another schematic exterior perspective view of the lead anchor of FIG. 2 from a different angle.
Figure 4B:
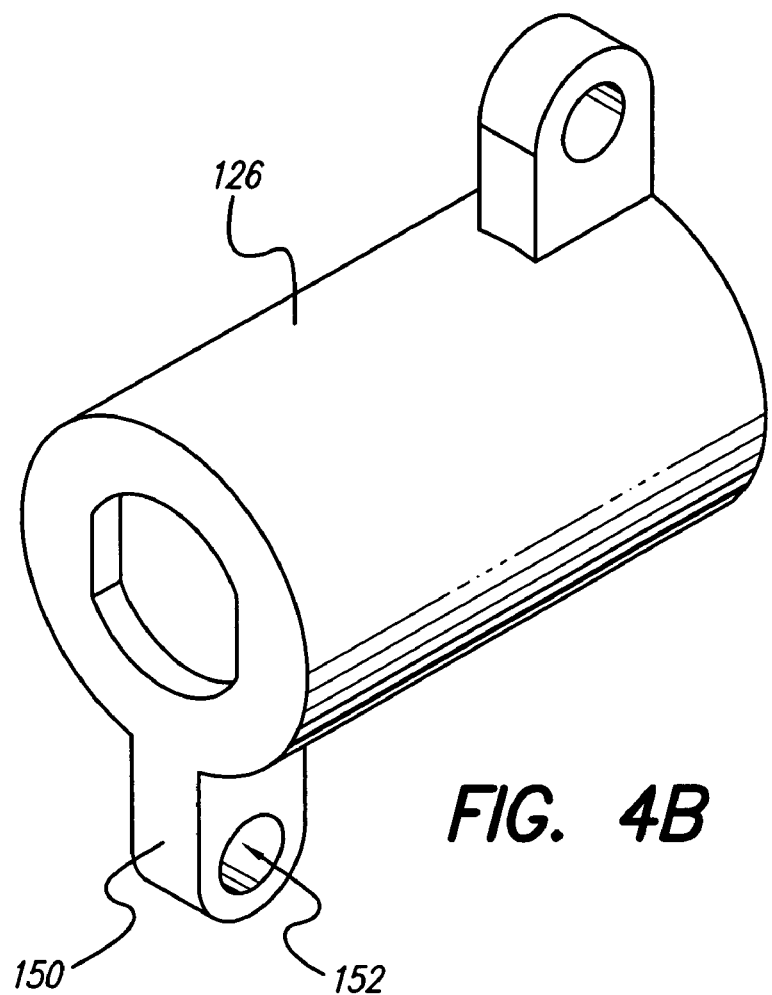
FIG. 4B is a schematic exterior perspective view from behind the lead anchor of FIG. 2.
Figure 4C:
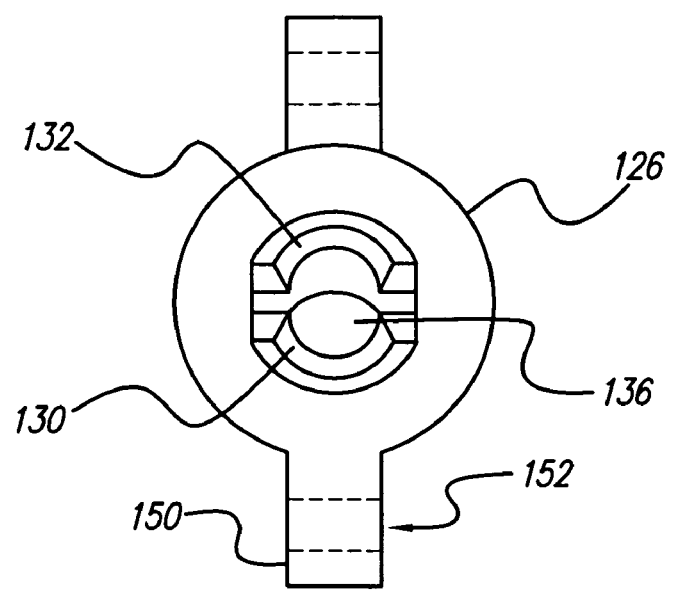
FIG. 4C is a schematic rear view of the lead anchor of FIG. 2.
Figure 5:
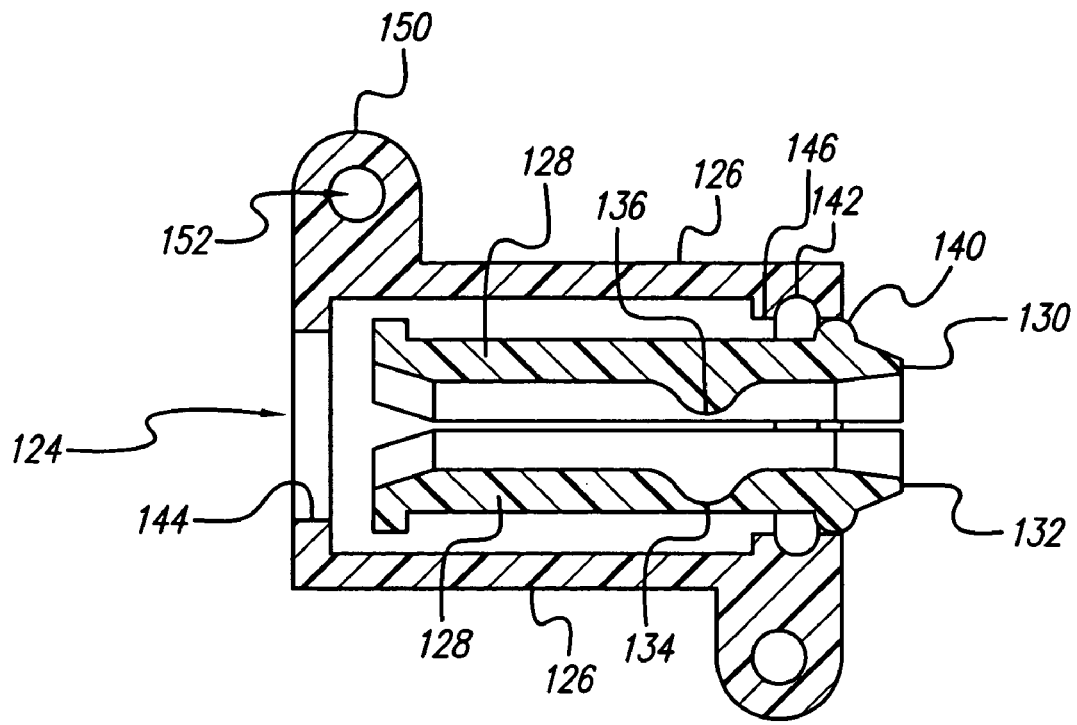
FIG. 5 is a schematic cross-sectional view of the lead anchor of FIG. 2.
Figure 6:
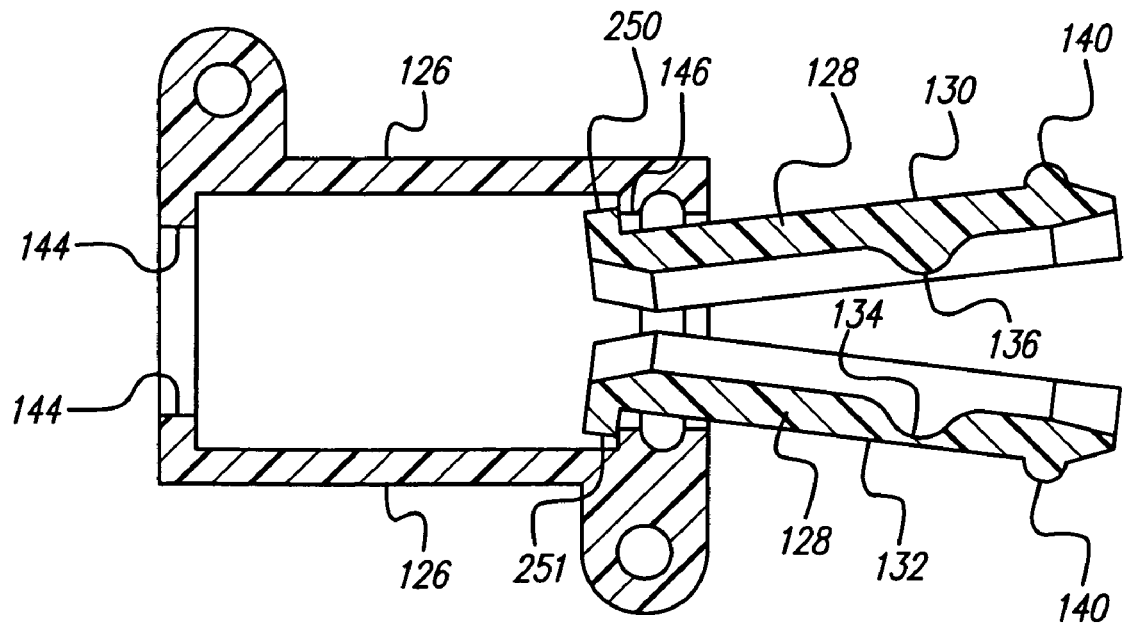
FIG. 6 is a schematic cross-sectional view of the lead anchor of FIG. 2 with the inner sleeve extended.

The locking projection 140 can be an annulus, or an annulus-like structure, of protruding material as illustrated in FIGS. 3 and 4 or can be one or more individual projections. Likewise, the locking indentation can be an annular arrangement or one or more individual indentations. Other locking arrangements can be used. One non-limiting example of such an arrangement includes tabs or ridges formed on the inner sleeve and outer housing which can be interlocked by aligning the tabs or ridges and then rotating the inner sleeve relative to the outer housing so that the tab(s) or ridge(s) on the outer housing cooperate with the tab(s) or ridges(s) on the inner sleeve to act as a stop to longitudinal movement of the inner sleeve within the outer housing. The outer surface of the inner sleeve 128 near opening 122 can be tapered, as illustrated in FIGS. 2, 5, and 6, to facilitate manual disengagement of the locking arrangement, if desired. Optionally, the inner surface of the inner sleeve 128 at one or both ends of the sleeve can be tapered (as illustrated in FIGS. 5 and 6). Tapering at one or both ends may facilitate guiding the lead 106 through the lead anchor 100 during initial installation and also facilitate the placement of the lead 106 through the two piece sleeve 128 extending out from outer housing 126, as shown in FIG. 6.

The outer housing 126 can optionally include a protruding portion 146, as illustrated in FIGS. 5 and 6, near or at the opening 122 to act as a stop and prevent or hinder the inner sleeve 128 from being completely removed from the outer housing. The locking indentation 142 (or locking protrusion) can be provided in the protruding portion 146 (as illustrated in FIGS. 5 and 6), if desired. The inner sleeve may also include stops 250, 251 (FIG. 6) that cooperate with the protruding portion 146 to prevent or hinder complete removal of the inner sleeve 128 from the outer housing 126.

Optionally, a stop 144 can be formed on the inner surface of the outer housing 126 to stop the inner sleeve 128 from being pushed out of the opposing end 124 of the outer housing 126. The stop 144 can be an annular projection or can be one or more individual projections. The stop 144 is often formed at or near an end of the outer housing 126. In some embodiments, the stop 144 cooperates with optional stops 250, 251 to prevent or hinder the inner sleeve 128 from being pushed out of the outer housing 126. In some embodiments, the stop 144 can be formed by creating a non-circular opening in the end 124 of the outer housing 126, as illustrated in FIGS. 4B and 4C.

The lead anchor 108 preferably includes one or more suture openings that allow sutures to be used to fasten the lead anchor to surrounding tissue. In the illustrated example, the body 120 includes one or more (in the illustrated example, two) extensions 150 from the outer housing 126. These extensions 150 define openings 152 through which a suture can be made.

The outer housing 126 and inner sleeve 128 are typically formed using a rigid plastic material. Preferably, this material is biocompatible, durable, and suitable for implantation in a patient over an expected period of time. Examples of suitable materials include polysulfone, polyolefins, polypropylene homopolymers and copolymers, teflon, and polyetheretherketone. The inner sleeve 128 may be somewhat flexible to assist spreading, if the spreading is due to compression of a portion of the inner sleeve by the outer housing as another portion of the inner sleeve extends out of the outer housing.

The outer housing 126 and inner sleeve 128 can be formed using an available technique including, for example, molding techniques.

The length of the lead anchor 108 can be selected for the particular purpose. In some embodiments, for example, for spinal cord stimulation, the lead anchor may have a length in the range of 4 to 10 millimeters. This length may be shorter or longer than other available lead anchors, depending on the specific application. In an example operation of the lead anchor, a lead anchor 106 may be provided with the locking indentation 142 and locking projection engaged, as illustrated in FIG. 5. The inner sleeve 128 is pushed through, for example, from opening 124, the outer housing 126 so that a portion of the inner sleeve 128 extends out of the outer housing 126, as illustrated in FIG. 6. As the portion of the inner sleeve 128 extends out of the outer housing 126, the members 130, 132 spread apart and provide more space between the protrusion 136 and depression 134. The lead 106 can then be threaded through the body 120 of the lead anchor 108 and between the members 130, 132. The inner sleeve 128 can then be pushed back into the outer housing 126 so that the protrusion 136 and depression 134 engage the lead 106 and form a non-linear (for example, curved) path for the lead 106, as illustrated in FIG. 7. The inner sleeve 128 can continue to be pushed into the outer housing 126 until the locking projection 140 and locking indentation 142 engage to lock the inner sleeve within the outer housing. The lead anchor 106 can then be sutured to surrounding tissue using the suture openings 152.

To remove the lead 106 from the lead anchor 108, the members 130,132 can be squeezed together to disengage the locking projection 140 from the locking indentation 142. The inner sleeve 126 can then be pushed through opening 122 of the outer housing 126 so that a portion of the inner sleeve extends out of the outer housing and the members 130, 132 separate allowing the lead to be removed.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
   a body defining a first opening and a second opening through which a lead can pass, wherein the body comprises an outer housing and an inner sleeve, wherein the outer housing defines a lumen through which the lead can pass, and wherein the inner sleeve is slidably engaged with the outer housing on an axis that is parallel to the lumen of the outer housing; and
   a protrusion and a corresponding depression within the body and defined by the inner sleeve, wherein the corresponding depression is opposite the protrusion on the inner sleeve and the protrusion and depression cooperate to form a non-linear path, as defined by a longitudinal line along the center of the lead, for the lead through the body to resist movement of the lead within the lead anchor.

2. The lead anchor of claim 1, wherein the inner sleeve is cylindrical.

3. The lead anchor of claim 1, wherein the inner sleeve comprises a first member and a second member configured and arranged to spread apart from each other when the inner sleeve extends out of the outer housing partially, but less than fully, in order to receive the lead.

4. The lead anchor of claim 3, wherein the protrusion is defined in the first member of the inner sleeve and the depression is defined in the second member of the inner sleeve.

5. The lead anchor of claim 3, wherein the first member and the second member are separate.

6. The lead anchor of claim 1, wherein the inner sleeve has an outer surface and the outer housing has an inner surface that is in contact with at least a portion of the outer surface of the inner sleeve and wherein a one of the outer surface and the inner surface defines a locking indentation and an other of the outer surface and the inner surface defines a corresponding locking projection, wherein the lead anchor is configured and arranged so that the inner sleeve can be moved within the outer housing to engage the locking indentation and locking projection and, thereby, resist further movement of the inner sleeve within the outer housing.

7. The lead anchor of claim 6, wherein at least one of the inner surface of the outer housing or the outer surface of the inner housing comprises a stop projection formed thereon to limit the movement of the inner sleeve out of one of the first and second openings.

8. The lead anchor of claim 1, wherein the outer housing has an inner surface that is in contact with at least a portion of the inner sleeve and wherein the inner surface has a stop projection formed therein to limit the movement of the inner sleeve out of one of the first and second openings.

9. The lead anchor of claim 8, wherein the inner sleeve has an outer surface that is in contact with at least a portion of the outer housing and wherein the outer surface has a stop projection formed thereon to limit the movement of the inner sleeve out of one of the first and second openings.

10. The lead anchor of claim 1, wherein the depression is larger than the protrusion.

11. The lead anchor of claim 1, wherein the body defines at least one suture opening.

12. The lead anchor of claim 1, wherein the lead anchor comprises a plurality of protrusions and a plurality of corresponding depressions.

13. An implantable stimulation device, comprising:
   a control module;
   an electrode array;
   a lead coupling the control module to the electrode array; and
   at least one lead anchor disposed around a portion of the lead, wherein the lead anchor comprises
      a body defining a first opening and a second opening through which the lead can pass, wherein the body comprises an outer housing and an inner sleeve, wherein the outer housing defines a lumen through which the lead can pass, and wherein the inner sleeve is movably engaged with the outer housing on an axis that is parallel to the lumen of the outer housing; and
      a protrusion and a corresponding depression within the body and defined by the inner sleeve, wherein the corresponding depression is opposite the protrusion on the inner sleeve and the protrusion and depression cooperate to form a non-linear path, as defined by a longitudinal line along the center of the lead, for the lead through the body to resist movement of the lead within the lead anchor.

14. The implantable stimulation device of claim 12, wherein the implantable stimulation device is a spinal cord stimulator.

15. A method of implanting an implantable stimulation device, the method comprising:
   implanting an electrode array near tissue to be stimulated;
   implanting a control module;
   coupling the electrode array to the control module using a lead;
   anchoring the lead to the surrounding tissue using a lead anchor, wherein the lead anchor comprises a body defining a first opening and a second opening through which the lead can pass and a protrusion and a corresponding depression within the body that cooperate to form a non-linear path, as defined by a longitudinal line along the center of the lead, for the lead through the body to resist movement of the lead within the lead anchor, wherein the corresponding depression is opposite the protrusion, wherein the body comprises an outer housing and an inner sleeve and the protrusion and depression are defined by the inner sleeve, wherein the outer housing defines a lumen through which the lead can pass, and wherein the inner sleeve is movably engaged with the outer housing on an axis that is parallel to the lumen of the outer housing.

16. The method of claim 15, wherein anchoring the lead to the surrounding tissue comprises
   partially, but less than fully, extending the inner sleeve out of the outer housing to further separate the protrusion and depression,
   threading the lead through the body and between the protrusion and depression, and
   moving the inner sleeve back into the outer housing and engaging the lead with the protrusion and depression to form a non-linear path for the lead through the lead anchor.

17. The method of claim 16, wherein the inner sleeve comprise a first member and a second member and extending a portion of the inner sleeve out of the outer housing comprises increasing a separation distance between a first end of the first member and a first end of the second member as the inner sleeve extends partially, but less than fully, out of the outer housing to receive the lead.

18. The method of claim 16, wherein anchoring the lead to the surrounding tissue further comprises engaging a locking projection disposed on a one of the inner sleeve and outer housing with a locking indentation disposed on an other of the inner sleeve and outer housing.

19. The method of claim 18, further comprising removing the lead from the lead anchor by squeezing the inner sleeve to disengage the locking projection from the locking indentation and extending a portion of the inner sleeve out of the outer housing to further separate the protrusion and depression.

20. The method of claim 15, further comprising removing the lead from the lead anchor.

* * * * *